US00PP23005P3

(12) United States Plant Patent
Harris et al.

(10) Patent No.: US PP23,005 P3
(45) Date of Patent: Sep. 4, 2012

(54) AZALEA PLANT NAMED 'MNIHAR013'

(50) Latin Name: ***Rhododendron* sp.**
Varietal Denomination: MNIHAR013

(75) Inventors: James O. Harris, Lawrenceville, GA (US); Ella Ruth Harris, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 142 days.

(21) Appl. No.: 12/807,054

(22) Filed: Aug. 25, 2010

(65) Prior Publication Data

US 2012/0054927 P1 Mar. 1, 2012

(51) Int. Cl.
*A01H 5/00* (2006.01)

(52) U.S. Cl. ..... Plt./238

(58) Field of Classification Search ..... Plt./238
See application file for complete search history.

*Primary Examiner* — Kent L Bell
(74) *Attorney, Agent, or Firm* — Jondle & Associates, P.C.

(57) ABSTRACT

A new and distinct variety of Azalea plant with spring and fall blooming, attractive, showy, single orange-red flowers, easily propagated by semi-hardwood cuttings in late spring through summer, moderate growth rate under normal fertilization and moisture conditions; broadly-rounded and freely-branching in habit, grows well in containers, thrives in shade or sun and is hardy in Zone 6, is disclosed.

2 Drawing Sheets

Genus and species: *Rhododendron* sp.
Variety denomination: 'MNIHAR013'.

BACKGROUND OF THE NEW PLANT

The present invention is a new and distinct variety of evergreen Azalea of the genus *Rhododendron*. This new Azalea, hereinafter referred to as 'MNIHAR013', was discovered in 2003 in Lawrenceville, Ga. 'MNIHAR013' originated from a planned cross hybridization between the female azalea plant 'Conleb' (U.S. Plant Pat. No. 10,581) and the male azalea plant 'September Morn' (unpatented) in a controlled environment in Lawrenceville, Ga. The instant plant has attractive, showy, orange-red flowers, a broadly-rounded, airy growth habit, and cold hardiness.

The new variety was first propagated via semi-hardwood cuttings in 2003 in Dearing, Ga. and has been asexually reproduced repeatedly by semi-hardwood cuttings in Dearing, Ga. for over seven years. 'MNIHAR013' has been found to retain its distinctive characteristics through successive asexual propagations via semi-hardwood cuttings.

'MNIHAR011' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, orange-red flowers;
3. Numerous single flowers;
4. Easily propagated by semi-hardwood cuttings in late spring through summer;
5. Moderate growth rate under normal fertilization and moisture conditions;
6. Broadly-rounded, airy in nature;

7. Grows well in containers;
8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of 6-year-old plants grown in filtered shade in 2008 and 2009 in Dearing, Ga.

DETAILED BOTANICAL DESCRIPTION OF THE NEW PLANT

Figure 1:
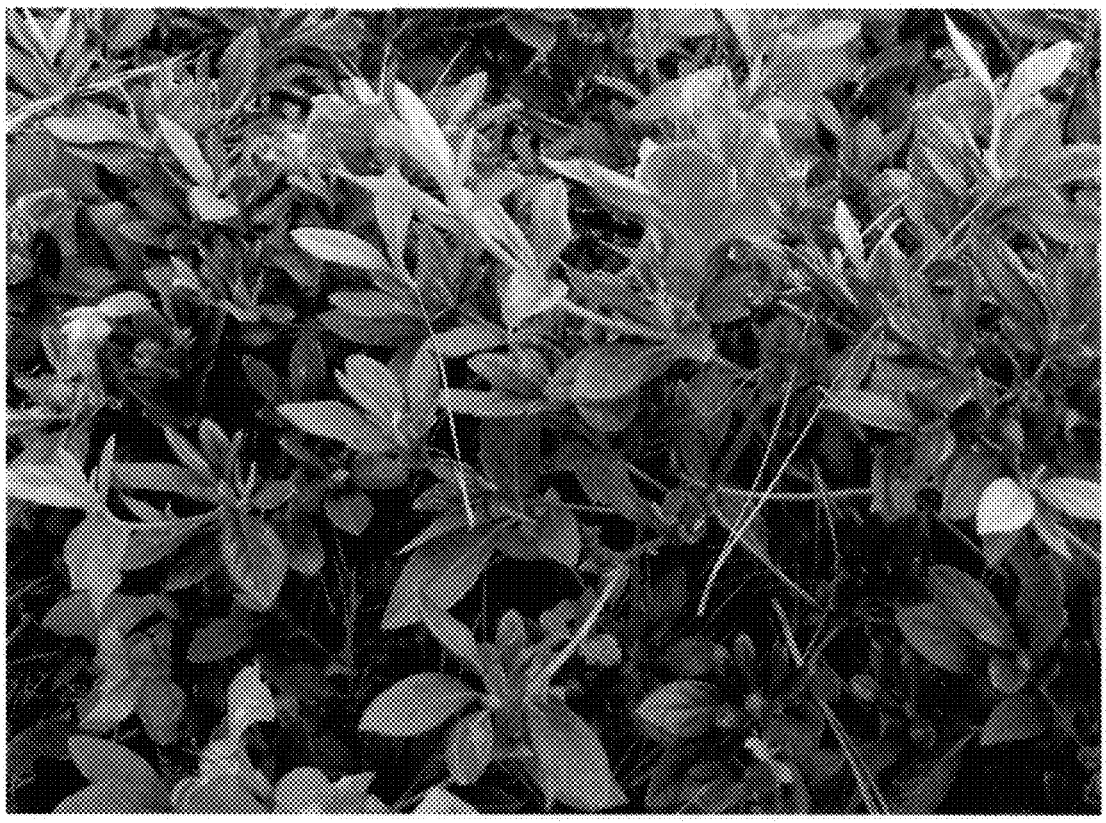
FIG. 1 is a close-up showing stems, mature foliage, and flowers.
Figure 2:
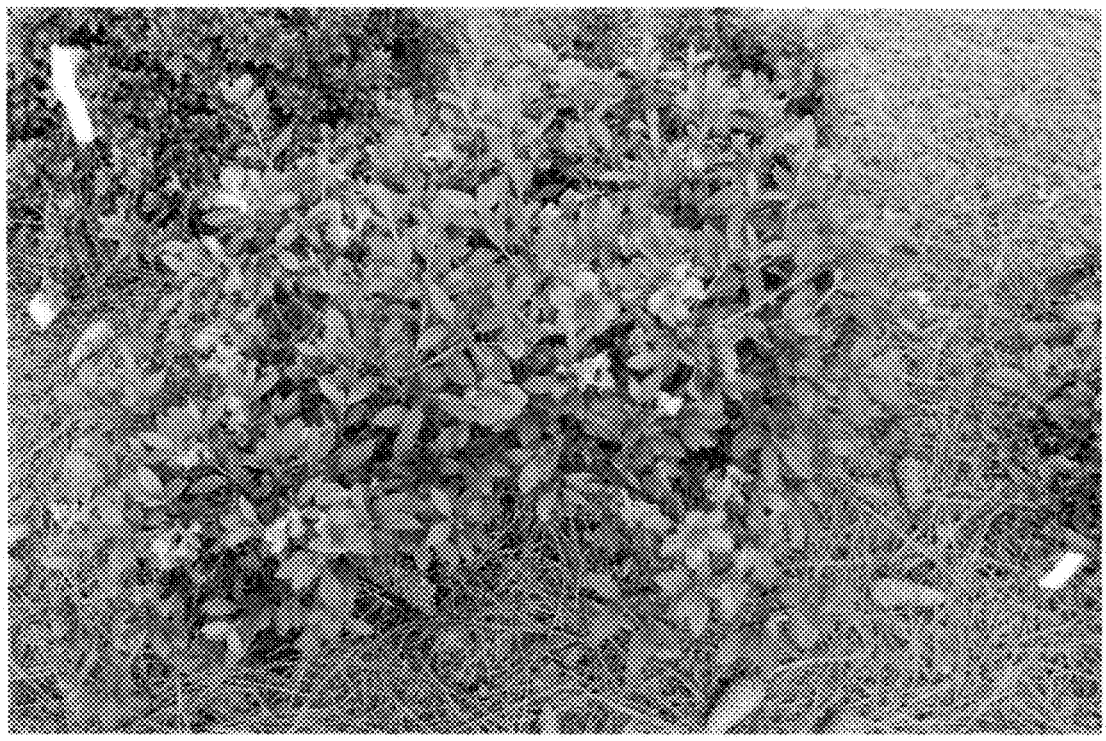
FIG. 2 shows the growth habit of a whole plant that is six years old.
Figure 3:
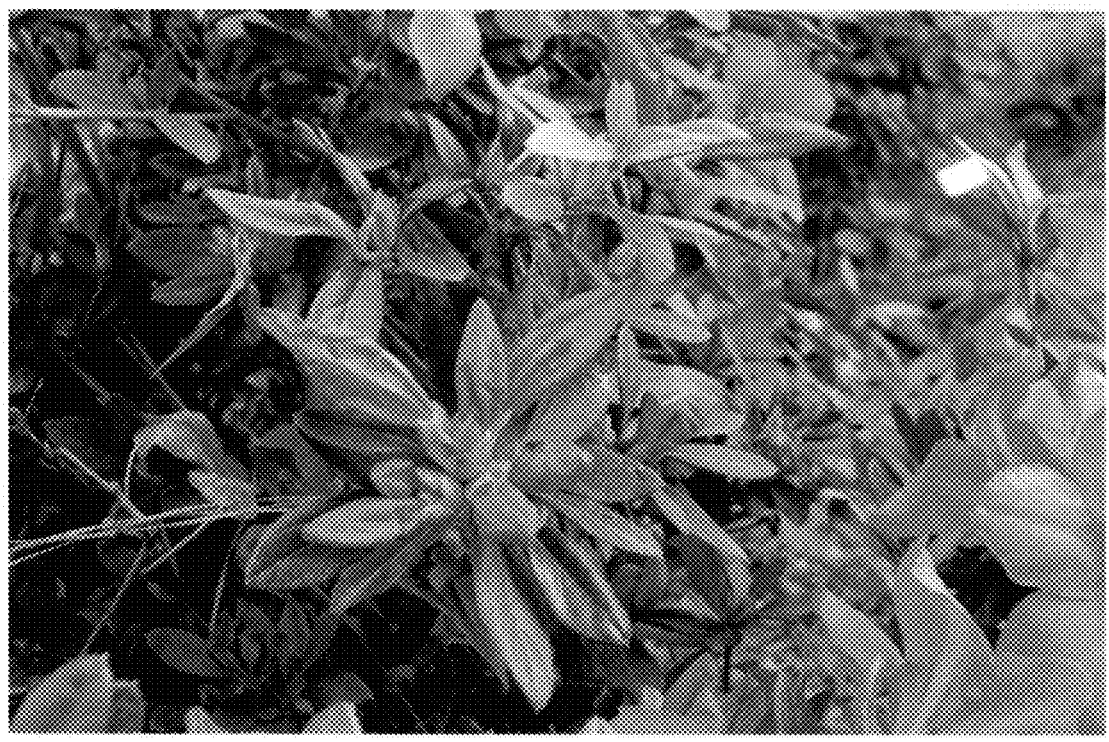
FIG. 3 is a close-up showing flower buds and some immature foliage.
Figure 4:
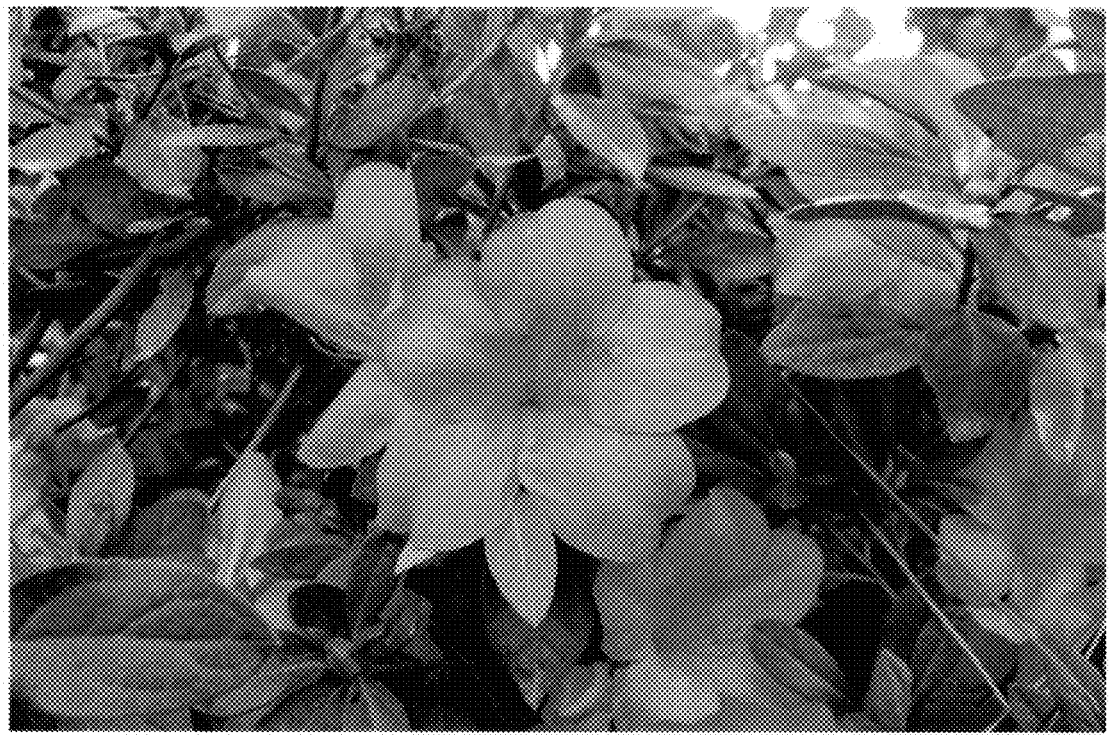
FIG. 4 is a close-up showing flower size, form, and color.

The following is a detailed description of 'MNIHAR013' based on observations made of 4-year-old plants grown in three-gallon containers according to wholesale commercial production conditions, under full-sun, and in an evaluation bed under semi-shade conditions in Dearing, Ga. in the winter, spring, summer, and fall seasons of 2009. The colors of the various plant parts are detailed with reference to The Royal Horticultural Society Colour Chart (2001).

Classification:

*Family*.—Ericaceae.
*Species*.—*Rhododendron* sp.
*Common Name*.—Azalea.
*Commercial name*.—'MNIHAR013'.

Parentage:

*Female parent*.—The azalea plant 'Conleb' (U.S. Plant Pat. No. 10,581).

*Male parent*.—The azalea plant 'September Morn' (unpatented).

Growth:

*Form*.—Broadly-rounded, airy in nature.

*Texture*.—Medium.

*Height*.—91.44 cm to 121.92 cm.

*Width*.—121.92 cm to 152.4 cm.

*Growth habit*.—Broadly-rounded and freely-branching.

*Growth rate*.—Moderate growth rate under normal fertilization and moisture conditions. In a period of six years from a rooted cutting the plant reaches a height of 76.2 cm and a spread of 106.68 cm. The growth rate is normally about 12 cm per year; the plant reaches a height of 91.44 cm to 121.92 cm at maturity while maintaining a dense habit due to the abundant branch development.

*Spring growth*.—The date of initial spring growth is March 15, followed by continuous growth through fall.

*Life cycle*.—Perennial and evergreen.

Leaves:

*Arrangement*.—Alternate, simple, pubescent, and evergreen.

*Shape*.—Elliptic to broadly elliptic.

*Apex*.—Mucronate.

*Base*.—Acute to acuminate.

*Margin*.—Entire.

*Length*.—2.6 cm.

*Width*.—1.3 cm.

*Venation pattern*.—Pinnate. Mid-veins and laterals: Upper surface: Impressed. Lower surface: Prominent.

*Immature leaf*.—Upper surface: Color: Matte RHS 144A (Yellow-green) with RHS 59A (Red-purple) along margin. Pubescence: Villous mainly along the margin and midvein. Pubescence color: RHS N159D (Orange-white) to RHS 159A (Orange-white). Lower surface: Color: Matte RHS 146C (Yellow-green). Pubescence: Villous to strigose along margin and midvein. Pubescence color: RHS N155A (White) to RHS 159A (Orange-white).

*Mature leaf*.—Upper surface: Color: Matte RHS 139A (Green). Pubescence: Strigose. Pubescence length: 0.1 cm. Pubescence color: RHS 166D (Greyed-orange). Lower surface: Color: Matte RHS 146A (Yellow-green). Pubescence: Strigose concentrated around mid-vein. Pubescence length: 0.1 cm. Pubescence color: RHS 166D (Greyed-orange).

*Petiole*.—Length: 0.5 cm. Diameter: 0.125 cm×0.1 cm. The petiole is not perfectly round and is a bit flattened. Color: Immature: RHS 145B (Yellow-green). Mature: RHS 146C (Yellow-green). Pubescence: Strigose. Pubescence length: 0.015 cm. Pubescence color: Immature: RHS N159D (Orange-white). Mature: RHS 166B (Greyed-orange).

Stems:

*Form*.—Densely branched at buds.

*Young stems* (*1 year old and younger*).—Color: RHS 144B (Yellow-green). Pubescence: Strigose. Pubescence color: RHS N155A (White) to RHS 167C (Greyed-orange).

*Second-year stems*.—Color: RHS 156A (Greyed-orange) and RHS 201A (Grey). Pubescence: Strigose. Pubescence color: RHS 165A (Greyed-orange). Length: 12.0 cm with occasional stems reaching 16.0 cm in length. Diameter: 0.4 cm. Pith: Solid and uniform. Internode length: Average 2.25 cm.

Flower buds:

*Arrangement and form*.—Tight; persistent; borne in groups of one or two sheathed by a pair of modified leaf bracts. Length: 1.9 cm. Width: 0.9 cm. Color: Apex: RHS 143C (Green). Base: RHS 145B (Yellow-green).

*Shape*.—Ovate.

*Apex*.—Acuminate.

*Base*.—Rounded.

*Length* (*at tight bud*).—2.0 cm.

*Diameter* (*at tight bud*).—0.7 cm.

*Color* (*of scales*).—Immature: RHS 145C (Yellow-green). Mature: RHS 145B (Yellow-green).

*Texture*.—Pubescent; tomentose to villous pubescence. Pubescence color: RHS 167B (Grey-orange).

*Pedicel*.—Length: 1.0 cm. Diameter: 0.125 cm. Texture: Tomentose pubescence. Pubescence color: RHS N155A (White). Color: RHS 44D (Red).

*Calyx*.—Form and arrangement: Composed of 5 sepals in a cup-shape. Length: 0.4 cm. Width: 0.4 cm. Pubescence: Tomentose. Pubescence color: RHS N155A (White). Sepals: Shape: Broadly elliptical. Apex: Cuspidate to obtuse. Base: Fused; joined at base to form a cup. Margin: Entire with some lobulate. Color: Upper surface: RHS 144C (Yellow-green). Lower surface: RHS 143B (Green). Length: 0.5 cm. Width: 0.25 cm.

Flowers:

*Type*.—Perfect, single flowers.

*Shape*.—Open funnel-shaped.

*Flowering habit and period*.—Borne on the current season's growth; 2 to 3 weeks beginning in late March to early April in Dearing, Ga.; flowering resumes in August and continues until frost.

*Lastingness of flowers on the plant*.—4 to 7 days in the sun; 6 to 9 days in the shade.

*Fragrance*.—Absent.

*Diameter*.—5.4 cm.

*Depth*.—2.8 cm.

*Petals*.—Quantity per flower and arrangement: 5 imbricate petals that are fused at the base and remain fused up to 1.3 cm from the base and 2.3 cm from the base for the three petals with spots. Shape: Obovate. Apex: Rounded. Base: Fused. Margin: Entire and wavy. Texture (both upper and lower surfaces): Glabrous. Length: 4.0 cm. Width: 2.1 cm. Color: Upper surfaces: RHS N34C (Orange-red). Lower surfaces: RHS 44D (Red) to N34A (Orange-red); with spots, the upper surface of the spots are RHS N34A (Orange-red) and lower surface of spots are not visible.

Reproductive parts:

*Pistil*.—Quantity and form: Single, non-petaloid. Length: 4.5 cm. Diameter: 0.05 cm. Stigma: Color: RHS 46D (Red). Diameter: 0.075 cm. Style color: RHS 54B (Red). Ovary: Pubescent, tomentose with 5 locules. Pubescence color: RHS N155A (White).

*Stamens*.—Number: 7 to 10 per flower. Length: 3.7 cm. Color: RHS 54B (Red). Anther: Length: 0.2 cm. Width: 0.1 cm. Color: RHS 178D (Greyed-red). Pollen: Abundant. Pollen color: RHS 155B (White).

Fruit:

*Maturity*.—The capsule matures in about 6 months in Dearing, Ga. and the fruit set is low and contains about 100 to 300 non-winged seeds.

*Length*.—1.5 cm.

*Width*.—0.9 cm.

*Color*.—RHS 146A (Yellow-green).

CULTURE

'MNIHAR013' grows well in a wide range of conditions and tolerates sun to shade. 'MNIHAR013' prefers moist, well-drained soil that is rich in organic matter and responds well to mulching and medium applications of fertilizer. 'MNIHAR013' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, 'MNIHAR013' is compared to parental varieties 'Conleb' (U.S. Plant Pat. No. 10,581) and 'September Morn' (unpatented) and lists the differences between the varieties.

TABLE 1

| Characteristic | 'MNIHAR013' | 'Conleb' | 'September Morn' |
|---|---|---|---|
| Plant Height (Mature) | 91.44 cm to 121.92 cm | 121.92 cm to 152.4 cm | 76.2 cm |
| Flower Diameter | 5.4 cm | 6.5 cm | 5 cm to 6 cm |
| Flower Form | Single | Single to semi-double | Single |
| Flower Color | Orange-red | Red | Red |
| Bloom Period | Late-March to early April and August until frost | April and late July until frost | Early April and September until frost |
| Hardy Zone | 6 | 7 | 5 |
| Stamen Number | 7 to 10 | 0 to 9 | 5 |
| Stamen Type | Non-petaloid | Petaloid and non-petaloid | Non-petaloid |

When 'MNIHAR013' is compared to the commercial variety 'Roblen' (U.S. Plant Pat. No. 16,248), 'MNIHAR013' has faster, broader, and more open growth habit then 'Roblen' (i.e., 'MNIHAR013' has a height of 76.2 cm and spread of 106.68 cm in six years, whereas 'Roblen' has a height of 91.44 cm and a spread of 60.96 cm in six years). Additionally, 'MNIHAR013' produces orange-red flowers, while 'Roblen' has bright red flowers.

I claim:

1. A new variety of Azalea plant named 'MNIHAR013' as herein shown and described.

* * * * *